United States Patent [19]
Robertson

[11] Patent Number: 5,352,455
[45] Date of Patent: Oct. 4, 1994

[54] CONTROLLED RELEASE COMPOSITIONS

[75] Inventor: Steven Robertson, Strathclyde, Scotland

[73] Assignee: British Technology Group Ltd., London, England

[21] Appl. No.: 821,946

[22] Filed: Jan. 17, 1992

[30] Foreign Application Priority Data

Jan. 23, 1991 [GB] United Kingdom ............... 9101502

[51] Int. Cl.$^5$ ............................................. A61K 9/02
[52] U.S. Cl. .................................... 424/436; 424/486
[58] Field of Search ........................ 424/489, 486, 436

[56] References Cited

U.S. PATENT DOCUMENTS

| | | | |
|---|---|---|---|
| 4,767,627 | 8/1988 | Caldwell | 424/426 |
| 4,837,111 | 6/1989 | Deters | 424/436 |
| 5,079,009 | 1/1992 | Embrey | 424/486 |

FOREIGN PATENT DOCUMENTS

| | | |
|---|---|---|
| 2047093 | 3/1979 | United Kingdom . |
| 2047094 | 3/1979 | United Kingdom . |

Primary Examiner—Thurman K. Page
Assistant Examiner—William E. Benston, Jr.
Attorney, Agent, or Firm—Nixon & Vanderhye

[57] ABSTRACT

Controlled release compositions comprising a water swellable carrier and an active material having crenellated surface exhibit improved release properties. Suppositories and pessaries of generally cylindrical shape having four or five crenellations spaced equally around the perimeter and extending substantially along the length of the cylinder are preferred. Suppositories comprising four or five rounded crenellations which release morphine sulphate are especially useful.

8 Claims, 3 Drawing Sheets

CONTROLLED RELEASE COMPOSITIONS

This invention relates to compositions designed to release an active ingredient into an aqueous medium in a controlled manner.

A considerable number of proposals to use carriers especially polymeric carriers in the formulation of controlled release compositions exist in the art. In their simplest form these compositions release their active contents at a rate which is proportional to $t^{\frac{1}{2}}$ where t is the time elapsed since the device was exposed to the aqueous medium. This is essentially due to the increase in the diffusion path length which the active material must traverse before being released with time. Such devices are not ideal since the rate of release drops to a level which may not be satisfactory relatively quickly. One method which has been proposed to alleviate this problem is to control the geometry of the device. One such device is described in U.S. Pat. No. 3,924,622. The geometry is such that as the diffusion path length increases there is an increase in the area of the carrier comprising the active which is exposed to the aqueous medium.

Another method by which this problem may be alleviated is the utilisation of carrier materials which alter their geometry when exposed to water. The most common class of carriers which have been proposed are water swellable materials. They are advantageous in that the initial release of active is effectively slowed as the materials swells and presents the active with a diffusion path length which is more nearly constant. A particular example of a material which has been proposed for use are the water swellable cross-linked poly(ethylene oxide) hydrogels which are described in British Patent Applications 2047093 and 2047094. These disclosures suggest that the hydrogels can be utilised in a variety of geometries for example as hollow or blank cylinders, spheres, tablets or slabs. Hollow devices especially hollow cylindrical devices are clearly attractive insofar as the diffusion path length cannot exceed the thickness of the cylinder wall. However, such devices are disadvantageous insofar as they may be difficult to fabricate and in that ideally the ends of the cylinders will be closed so as to prevent release from the interior walls thus complicating the fabrication of the device still further. It will be appreciated that there remains a need to provide controlled release compositions which have improved release profiles and are reasonably simple to produce.

We have now discovered that compositions having improved release properties may be produced by fabricating the carrier in a form which has a series of crenellations on the surface.

Accordingly, from one aspect this invention provides a controlled release composition which comprises a carrier and at least one active agent which is characterised in that the surface of the composition is crenellated.

The nature of the crenellations may vary, in particular according to the basic shape of the composition. Thus, for example, where the composition is spherical the surface may be dimpled so as to be similar to that of a golf ball. Alternatively, the crenellations may be provided as pimples upon the surface of the sphere. Where the composition takes the shape of a cylinder or a slab, the crenellations may conveniently take the form of ridges or furrows running for convenience parallel to the longitudinal axis of the cylinder or slab. The crenellations may be arranged in a regular fashion or an irregular one. For example the ridges or furrows may be arranged so as to lie parallel or they may be at an angle to one another; they may be continuous or they may not. The crenellations will preferably have a depth which is significant in relation to the thickness of the device. In the preferred embodiments the entire surface of the composition will be crenellated and the depth of the crenellations will be such that the ratio of maximum dimension of the device to the minimum dimension measured in at least one direction will be at least 2:1. The crenellations will preferably be arranged and of such a shape as to increase the external surface area of the device by a factor of at least 15% or even at least 25% compared to a composition containing the same quantity of carrier but having a smooth surface and the same basic shape.

The elevated portions of the crenellations will be such that they comprise at least 30% and preferably at least 50% by weight of the total weight of the composition. The preferred compositions thus provide a controlled release composition having a large surface area and in which the crenellations ensure that the diffusion path length for at least that proportion of the active contained in the elevated portions is substantially constant.

The compositions of this invention are conveniently and preferably useful in the administration of pharmaceutically active compounds in human or animal patients. They may be utilised as oral dosage forms, as subcutaneous implants or as a buccal, cervical, intrauterine, nasal, dermal inserts or artificial gland device. They find particular application as suppositories or pessaries. The compositions may be fabricated in the sizes and shapes which are conventional for these applications. In the preferred embodiments the devices will conveniently take the form of slabs or cylinders having a longitudinal axis which is longer than their other axes and a relatively small cross sectional area. The invention will hereinafter be described in relation to such devices although it will be appreciated that other configurations could be employed.

The invention is illustrated in the accompanying drawings in which.

The cross-sectional area of the three devices is approximately equal, i.e. equal lengths of each cylindrical device will comprise equal amounts of material. The hollow cylindrical device of FIG. 3 typically has an internal diameter of 7 mm and an external diameter of 10 mm. The device of FIG. 1 has a maximum diameter A of 8.7 mm, a minimum diameter B of 3 mm. The diameter of the crenellations C is 3 mm. The radius D is 4.35 mm. The device of FIG. 2 has corresponding dimensions of 4 mm (B), 3 mm (C) and 4.15 mm (D).

The number of crenellations may vary but will preferably be from 3 to 6. The shape of the crenellations may also vary. They could be triangular, circular or even square. The crenellations will preferably be of equal size and will be spaced equiangularly around the axis of the composition. The upraised portion may have a greater width at its extremity than at its neck in which case the space between the crenellations may have a corresponding narrow neck and wide base. This latter construction may be particularly preferred in a further embodiment of the invention in which the space between crenellations is filled with a further composition which may be of therapeutic value. The space may be filled with other active materials optionally in admixture with a carrier or with another controlled release composition so as to provide a novel release profile of one or a combination of active materials.

Figure 1:
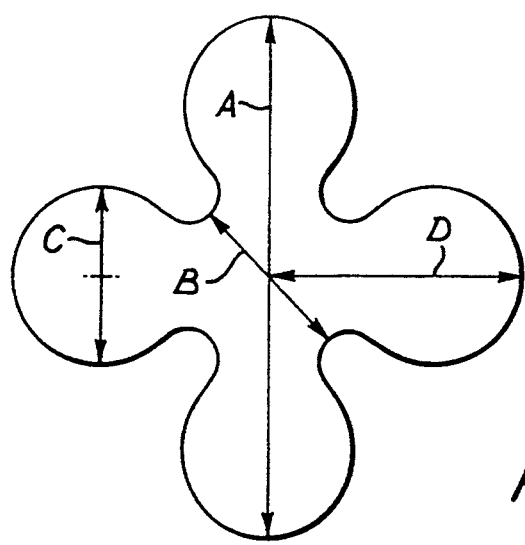
FIG. 1 is a cross-sectional view of a generally cylindrical device having four crenellations.
Figure 2:
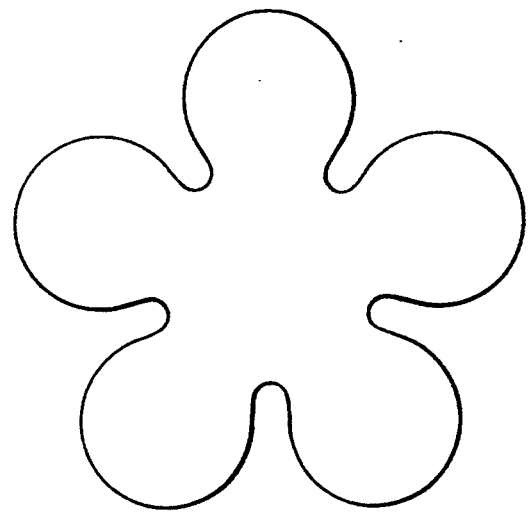
FIG. 2 is a cross-sectional view of a generally cylindrical device having five crenellations.

The devices shown in FIGS. 1 and 2 have a uniform cross section. It will be appreciated that this is not an essential feature of the devices of this invention. In practice the crenellations may spiral around the longitudinal axis of the cylinder or they may be interrupted and/or off-set against one another.

The devices of this preferred aspect of the invention need not have a cross-section which is perfectly cylindrical but may have ellipsoidal or in the extreme case a rectangular cross section.

In the preferred embodiments the devices have a solid cross section although devices having a hollow cross section may also be useful. However, those devices having a solid cross section are preferable especially insofar as they are relatively easy to fabricate compared to those having a hollow cross section, because they are relatively strong and because they offer a reduced overall cross-sectional area to the body.

The devices of this invention may be formed from any material which is known or has been proposed for use in the art of controlled release. The materials may conveniently be polymeric materials and in particular are preferably water swellable polymeric materials.

The carrier material should be one which can conveniently be fabricated in the crenellated shapes useful according to this invention. The fabrication may be carried out using any one of a variety of techniques known in the art which are useful for a particular carrier. The composition should retain its mechanical integrity over the period during which the active is to be released. The water swellable materials may alter their shape somewhat during that period but should retain a crenellated shape.

In an especially preferred embodiment the compositions are formed from the polymers which are described in GB 2047094, i.e. they are polymeric carriers comprising residues which are cross linked through urethane groups and which comprise polyethylene oxide having a ratio of number average molecular weight to functionality greater than 1000 and wherein the polymeric material is a crystalline hydrogel in the dry form and exhibits syneresis in the wet form.

The compositions of this invention find particular application in the form of suppositories and pessaries for the administration of pharmaceuticals in humans. They may be used to provide release over a period of up to 48 hours although longer periods of release of from 3 and up to 10 days may be attainable and desirable in some instances. The crenellations in the surface of the compositions offer an additional advantage in that they can be removed from the body more readily than those having a smooth surface if desired. The crenellations may also facilitate the location of a cord on the composition which in use extends outside the body and can be used to pull the composition out of the body.

The compositions of this invention may conveniently be formulated by forming the water swellable material in the desired shape, immersing the formed polymer in a solution of the active material, allowing the material to swell and subsequently drying the swollen polymer. Again the polymers of GB 2047093 and GB 2047094 are preferred because of the ease with which they can be formulated in this way.

We have discovered that the devices of this invention which are water swellable provide release profiles of active material which are more consistently reproducible than those offered by identical devices having a smooth surface when used in vivo, especially in humans. The crenellated surface appears to swell in a more reproducible manner when placed in an in vivo environment.

The present invention is of broad applicability in the formulation of active substances, particularly biologically active substances. Examples of classes of biologically active substances which may be incorporated in compositions of the present invention include pharmaceuticals, bacteriostats, viruscides, insecticides, herbicides, larvicides, fungicides, algaecides, nematocides, topical or dermatological agents, antifoulants, for marine growth prevention, enzymes and preservatives. Of particular interest are compositions of the present invention comprising, as biologically active substance, at least one pharmaceutical.

The compositions of this invention thus find wide application in medical and surgical, including veterinary, contexts and in horticulture and agriculture as well as outside these areas.

There is no necessity for the active substance to be water soluble although it will often possess some degree of water solubility; all that is required is that it is soluble to an extent commensurate with its desired concentration (which, in the case of a biologically active substance, is related to this activity) in the controlled release composition of this invention in the water or organic solvent used to swell the polymeric carrier on incorporation of the active substance therein.

Specific classes of drug which may be utilised in a controlled release composition of the invention include abortifacients, hypnotics, sedatives, tranquilisers, antipyretics, anti-inflammatory agents, anti-histamines, antitussives, anti-convulsants, muscle relaxants, anti-tumour agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression, anti-spasmodics, antiulcer agents, preparations containing various substances for the treatment of infection by pathogens including anti-fungal agents, for example metronidazole, antiparasitic agents and other anti-microbials, anti-malarials, cardiovascular agents, preparations containing hormones, for example androgenic, estrogenic and progestational hormones, notably steroids such as oestradiol, sympathomimetic agents, hypoglycaemic agents, contraceptives, nutritional agents, preparations containing enzymes of various types of activity, for example chymotrypsin, preparations containing analgesics, for example aspirin, and agents with many other types of action including nematocides and other agents of veterinary application. Mixtures of active substances may be incorporated into the polymeric carrier.

The active substances may be incorporated into the polymer with this in dispersed form but is more preferably incorporated into the polymeric carrier after this has been formed into an appropriate physical format. Accordingly, the usual procedure for incorporation of the biologically active substance is for the polymer, in suitable physical form, to be swelled using a solution containing the substance or substances to be incorporated. This solution may often be aqueous but may incorporate organic solvents for example alcohols such as ethyl alcohol in order to solubilise the substance and also in view of the improved swelling characteristics of such mixtures, and in some instances a completely non-aqueous organic solvent such as chloroform, methyl benzoate, butyrolactone or benzyl alcohol may be used. After swelling and absorption of the active substance, the release composition may be dried to remove the solvent or alternatively may be used in the swollen form. It has been found that the swelling procedure, and in particular the proportion of swelling relative to the original volume which is allowed to take place, can have a quite significant effect upon the subsequent behaviour of the release composition in vivo, even though it may be dried before use. Preferably, therefore, the degree of swelling during incorporation of the biologically active substance lies between 50 parts per hundred and 700 parts per hundred of the original dry volume, particularly between 200 and 500 parts per hundred.

Certain of the areas of pharmaceutical utility for compositions according to the present invention, such as the administration of hormones, drugs for the treatment of prophylaxis of various conditions, e.g. substances having activity against pathogenic micro-organisms, are particularly suited to vaginal or rectal administration of the active substance and pessaries are of especial interest in such contexts. The compositions may, however, be used for various localised application in other parts of the body such as the treatment of maladies of the mouth or eye, for example glaucoma. The compositions are also of interest for oral administration or in a topical patch to release a drug which can treat or be absorbed by the skin; and for use by implantation.

The concentration of active substance incorporated into the controlled release composition of this invention can range from very high to very low. Thus, if a liquid biologically active material, such as m-cresol which swells the polymer to more than 1,000 pph, were used also to swell the polymer, then the active species could comprise more than 90% by weight of the release composition. A liquid which swelled to 1,000 pph and contained 25% by weight of a drug could leave a loading of more than 70% by weight of the drug in the dry polymer, and 30% by weight loadings would be commonly attainable. Much lower loadings, e.g. 1.0% to 0.5% are also readily attainable.

Other uses for compositions of the present invention include the prevention of formation of slime such as algae in swimming pools by application of a slimicide (or algaecide) consequent upon the daytime temperature rise, and the inhibition of polymerisation through release of a polymerisation inhibitor in response to a temperature rise in stored polymerisable monomers. In these cases, the active substance absorbed in the swollen polyethylene oxide is a slimicide (or algaecide) and a polymerisation inhibitor respectively. Controlled release compositions of this invention, in dry form, are also of interest in relation to the beneficial effect on the storage stability of potentially unstable compounds by incorporation into a crystalline matrix.

The invention is illustrated by the following examples:

EXAMPLE 1

A crystalline poly (ethylene oxide) hydrogel according to the teachings of British Patents 2047093 and 2947094 was produced by reaction of One part by weight of a poly (ethylene glycol) having a number average molecular weight of 4000 (purchased as pharmaceutical grade PEG 4000 from the K. & K. Greef Company)

One part by weight of hexane triol 2.5 parts by weight of hexamethylene diisocyanate.

Figure 3:
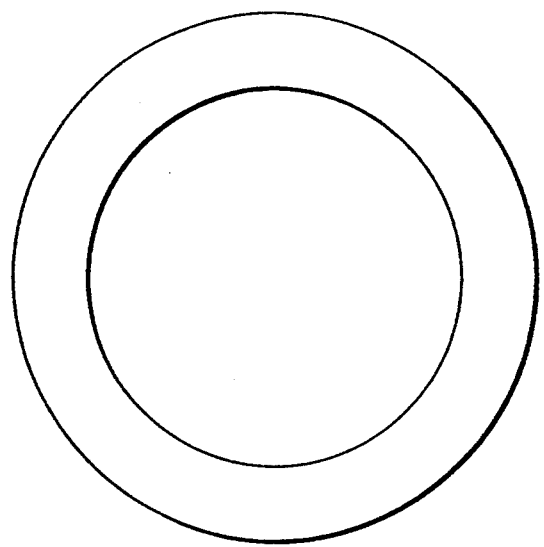
FIG. 3 is a cross-sectional view of a known hollow cylindrical device (which is included only for comparative purposes).
Figure 4:
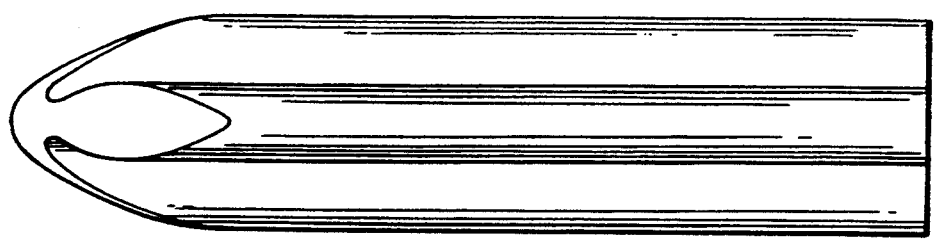
FIG. 4 is a side elevation of a device having the cross section shown in FIG. 1.
Figure 5:
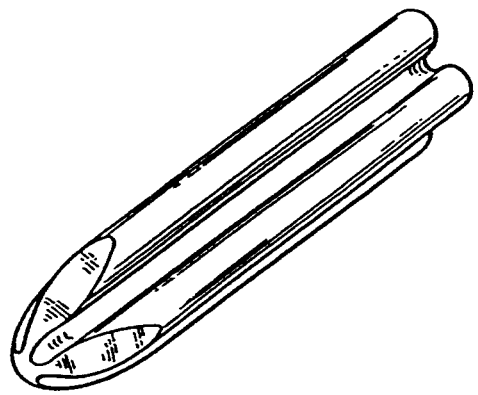
FIG. 5 is a perspective view of the device shown in FIG. 4.
Figure 6:
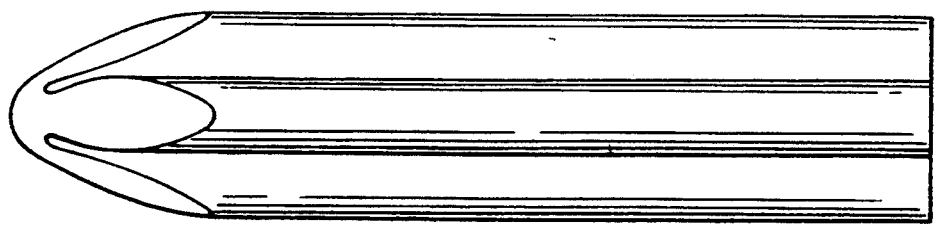
FIG. 6 is a side elevation of a device having the cross section shown in FIG. 2.
Figure 7:
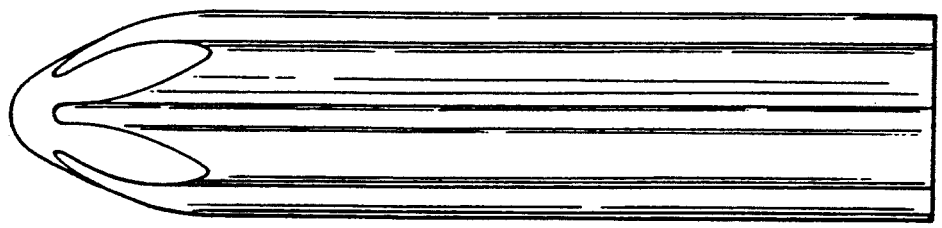
FIG. 7 is another side elevation of a device having the cross section shown in FIG. 2.
Figure 8:
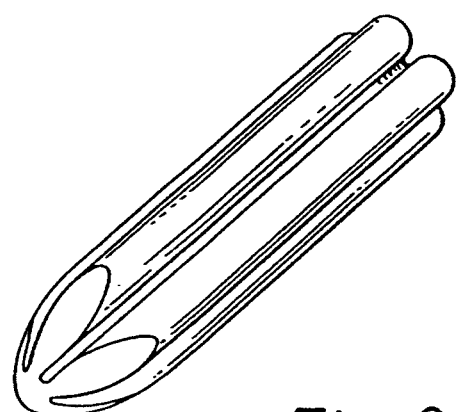
FIG. 8 is a perspective view of the device shown in FIGS. 6 and 7.

The reactants were polymerised in suitable moulds so as to produce a three separate solid polymers having the shapes illustrated in FIGS. 1, 2 and 3.

The compositions were cut to equal lengths. The compositions were immersed in an aqueous solution of morphine containing 30 gms/liter of morphine sulphate BP for a period of 24 hours. The swollen polymers were removed and dried under vacuum at ambient temperatures.

The release profile of these compositions was determined in a suitable pH 7.9 phosphate buffer using USP XX1 paddle method (a rotational speed of 50 rpm). Samples were withdrawn at appropriate time points and assayed in the ultraviolet spectrum at 210 nm. The results were as follows:

(1) Hollow Compositions (average of 3 results)

| Time (hours) | % Morphine Dissolved | CV % |
|---|---|---|
| 0.5 | 9.77 | 5.36 |
| 1.0 | 14.50 | 3.68 |
| 2.0 | 24.19 | 3.33 |
| 4.0 | 41.99 | 3.93 |
| 8.0 | 62.39 | 4.11 |
| 12.0 | 76.26 | 3.34 |

$T\frac{1}{2}$ = 5 hours 30 minutes.

(2) Four Ribbed Composition (average of 6 results)

| Time (hours) | % Morphine Dissolved | CV % |
|---|---|---|
| 0.5 | 33.93 | 2.72 |
| 1.0 | 40.18 | 1.76 |
| 2.0 | 52.13 | 1.97 |
| 4.0 | 72.55 | 1.67 |
| 8.0 | 90.02 | 1.29 |
| 12.0 | 90.42 | 1.15 |

$T\frac{1}{2}$ = 1 hour 45 minutes.

(3) Five Ribbed Composition (average of 6 results)

| Time (hours) | % Morphine Dissolved | CV % |
|---|---|---|
| 0.5 | 27.40 | 5.91 |
| 1.0 | 33.42 | 3.98 |
| 2.0 | 44.25 | 2.69 |
| 4.0 | 61.53 | 2.14 |
| 8.0 | 79.81 | 2.45 |
| 12.0 | 88.53 | 2.01 |

EXAMPLE 2

A second series of hollow compositions and four ribbed compositions were prepared loaded with morphine sulphate and tested in the manner described in Example 1. Each series comprised four suppositories made from different production batches of polymer. The results obtained are presented below.

(1) Hollow Compositions - % morphine sulphate dissolved.

| Time (hours) | 1 | 2 | 3 | 4 |
|---|---|---|---|---|
| 0.5 | 12.70 | 16.90 | 13.71 | 14.23 |
| 1.0 | 17.10 | 20.65 | 19.00 | 19.93 |
| 2.0 | 30.03 | 36.21 | 31.18 | 28.73 |
| 4.0 | 50.07 | 58.30 | 51.17 | 43.13 |
| 8.0 | 74.98 | 80.20 | 73.98 | 57.98 |
| 12.0 | 86.88 | 89.87 | 82.29 | 67.67 |

(2) Four Ribbed Compositions - % morphine sulphate dissolved.

| Time (hours) | 1 | 2 | 3 | 4 |
|---|---|---|---|---|
| 0.5 | 33.93 | 31.92 | 25.10 | 21.96 |
| 1.0 | 40.18 | 39.35 | 34.08 | 32.97 |
| 2.0 | 52.13 | 51.84 | 50.06 | 50.25 |
| 4.0 | 72.55 | 72.60 | 73.31 | 74.52 |
| 8.0 | 90.02 | 90.33 | 90.07 | 92.05 |
| 12.0 | 95.42 | 96.21 | 95.88 | 96.75 |

What is claimed is:

1. A controlled release composition which comprises a water swellable carrier and at least one active ingredient, said composition having a surface which is crenellated in the form of a series of furrows and ridges running in the direction of the longitudinal axis of a cylinder.

2. A composition according to claim 1, wherein the carrier is a water swellable polymeric material comprising residues which are crosslinked through urethane groups and which comprise polyethylene oxide having a ratio of number average molecular weight to functionality of greater than 1000 and wherein the polymeric material is a crystalline hydrogel in the dry form and exhibits syneresis in the wet form.

3. A composition according to claim 1, wherein the surface of the composition comprises from 3 to 6 crenellations.

4. A composition according to claim 3, wherein the surface comprises 4 crenellations.

5. A composition according to claim 3, wherein the surface comprises 5 crenellations.

6. A composition according to claim 3, wherein the crenellations are of equal size and are spaced equiangularly.

7. A composition according to claim 3, wherein the device has an external surface area which is at least 15% greater than that of a device formed from the same quantity of material having a smooth exterior surface.

8. A composition according to claim 3, wherein the active material is morphine.

* * * * *